US012697014B2

(12) United States Patent
Hasbun

(10) Patent No.: US 12,697,014 B2
(45) Date of Patent: Aug. 4, 2026

(54) MULTIPURPOSE HANDLE ASSEMBLY FOR USE WITH VARIED MEDICAL INSTRUMENTS

(71) Applicant: William Miguel Hasbun, Naples, FL (US)

(72) Inventor: William Miguel Hasbun, Naples, FL (US)

( * ) Notice: Subject to any disclaimer, the term of this patent is extended or adjusted under 35 U.S.C. 154(b) by 342 days.

(21) Appl. No.: 18/459,393

(22) Filed: Aug. 31, 2023

(65) Prior Publication Data

US 2024/0074639 A1      Mar. 7, 2024

Related U.S. Application Data

(60) Provisional application No. 63/374,499, filed on Sep. 2, 2022.

(51) Int. Cl.
| | |
|---|---|
| *A61B 1/00* | (2006.01) |
| *A61B 1/06* | (2006.01) |
| *A61B 1/227* | (2006.01) |
| *A61B 1/267* | (2006.01) |

(52) U.S. Cl.
CPC ...... *A61B 1/00105* (2013.01); *A61B 1/00066* (2013.01); *A61B 1/06* (2013.01); *A61B 1/227* (2013.01); *A61B 1/267* (2013.01)

(58) Field of Classification Search
CPC . A61B 1/227; A61B 1/233; A61B 2017/0046; A61B 2017/00477; A61B 1/267; A61B 1/06; A61B 1/00066; A61B 1/0692
USPC ................................................ 600/184–245
See application file for complete search history.

(56) References Cited

U.S. PATENT DOCUMENTS

| | | | |
|---|---|---|---|
| 2,289,226 A | 7/1942 | Allyn | |
| 3,978,850 A * | 9/1976 | Moore | A61B 1/227 600/249 |
| 4,006,738 A * | 2/1977 | Moore | A61B 1/07 385/119 |
| 4,147,163 A * | 4/1979 | Newman | A61B 1/00034 362/183 |
| 4,384,570 A | 5/1983 | Roberts | |
| 4,947,829 A | 8/1990 | Bullard | |
| 4,958,624 A | 9/1990 | Stone et al. | |
| 5,070,859 A | 12/1991 | Waldvogel | |
| 5,893,830 A | 4/1999 | Zeitels | |

(Continued)

*Primary Examiner* — Eduardo C Robert
*Assistant Examiner* — Tara Rose E Carter
(74) *Attorney, Agent, or Firm* — LaMorte & Associates, P.C.

(57) ABSTRACT

A handle assembly for a medical instrument, such as an otoscope, and the full assembly of the medical instrument. The handle assembly has a primary housing with a first end and an opposite open second end. The primary housing defines a central cavity. A standardized connector is formed at the first end. A detachable housing extension is attached to the opposite end. The housing extension defines an internal compartment that is accessible when detached. An otoscope head is provided that is sized to fit within the internal compartment. The otoscope head has a base, a neck, and a speculum support. The speculum support has a large open end, an opposite small open end, and a funnel shaped peripheral wall that extends there between. A slot is formed in the peripheral wall to enable secondary instruments to be manipulated within the speculum support.

12 Claims, 6 Drawing Sheets

(56)  References Cited

U.S. PATENT DOCUMENTS

| | | | | |
|---|---|---|---|---|
| 6,102,851 | A | 8/2000 | Mellin | |
| 6,217,512 | B1 * | 4/2001 | Salo | A61B 1/0607 |
| | | | | 600/179 |
| 7,771,350 | B2 | 8/2010 | Geist et al. | |
| 8,394,016 | B1 * | 3/2013 | Arne' | A61B 1/0684 |
| | | | | 600/193 |
| D984,643 | S | 4/2023 | Hasbun | |
| 11,617,502 | B2 | 4/2023 | Hasbun | |
| 2003/0018239 | A1 | 1/2003 | Cartledge | |
| 2003/0120131 | A1 | 6/2003 | Pecherer | |
| 2005/0165404 | A1 * | 7/2005 | Miller | A61B 10/025 |
| | | | | 606/80 |
| 2008/0300464 | A1 | 12/2008 | Dhingra | |
| 2009/0264708 | A1 | 10/2009 | Pacey et al. | |
| 2013/0023914 | A1 * | 1/2013 | Truong | A61B 1/015 |
| | | | | 606/162 |
| 2013/0245491 | A1 * | 9/2013 | Nikzad | A61B 1/227 |
| | | | | 600/555 |
| 2016/0128555 | A1 * | 5/2016 | McMahon | A61B 1/00071 |
| | | | | 600/200 |

* cited by examiner

MULTIPURPOSE HANDLE ASSEMBLY FOR USE WITH VARIED MEDICAL INSTRUMENTS

RELATED APPLICATIONS

This application claims the priority of U.S. Provisional Patent Application No. 63/374,499, filed Sep. 2, 2022.

BACKGROUND OF THE INVENTION

1. Field of the Invention

In general, the present invention relates to the structure of handles for laryngoscopes, otoscopes, and other handheld medical scopes. The present invention also relates to medical device handles that hold secondary objects and/or have multifunctional uses.

2. Prior Art Description

Many medical scopes have handles. For example, laryngoscopes have handles that attach to laryngoscope blades of various shapes and sizes. The connection used to attach each laryngoscope blade to the handle is standardized. The dimensions for the handle-to-blade connection are set forth in ISO 7376.7. Since the connection has standardized dimensions, any modern laryngoscope blade that complies to the standard can interconnect with any handle that also complies to that standard.

Handles that contain the standardized ISO 7376.7 connector are also capable of connecting to medical devices other than laryngoscope blades, provided those other medical devices use the standardized ISO 7376.7 connector dimensional standards. Accordingly, by customizing medical devices, such as otoscopes, tongue depressors, probes, and ophthalmic instruments, with a standardized ISO 7376.7 connector, a single handle can be utilized for a wide array of purposes.

Handles for medical instruments are intended to be held in an individual's hand. Since only the top of a handle contains the standardized ISO 7376.7 connector, there is typically extra room available in the handle. This extra room can be used to hold secondary devices. For instance, in U.S. Pat. No. 7,771,350 to Geist, a handle assembly is shown that holds batteries for a light. In U.S. Pat. No. 6,102,851 to Mellin, a handle assembly is shown that holds a removable pen light. The pen light is only operable once removed from the handle.

U.S. Pat. No. 11,617,502 to Hasbun, a handle assembly for a laryngoscope is shown that contains a light. However, the handle is dedicated to use on a laryngoscope and no other medical instrument.

The present invention is a specialized handle assembly that contains features that enable the handle to both hold secondary objects and to be used for more than one purpose with more than one medical instrument. The improved handle assembly enables a heath care worker to be more effective by being able to carry a larger arsenal of medical tools in a confined space. The details of the improvements provided by the present invention are described below.

SUMMARY OF THE INVENTION

The present invention is a handle assembly for a medical instrument, such as an otoscope, and the full assembly of the medical instrument with the handle assembly. The handle assembly has a primary housing that extends between a first end and an opposite open second end. The primary housing defines an open central cavity.

A standardized laryngoscope blade connector is formed at the first end of the primary housing. A selectively detachable housing extension is attached to the opposite end of the primary housing. The housing extension defines an internal compartment that is accessible when the housing extension is detached from the primary housing.

An otoscope head is provided that is sized to fit within the internal compartment of the housing extension. The otoscope head has a base, a neck, and a speculum support. The base is configured to interconnect with the laryngoscope blade connector at the first end of the primary housing. The speculum support has a large open end, an opposite small open end, and a funnel shaped peripheral wall that extends from the large open end to the small open end. A slot is formed in the peripheral wall to enable secondary instruments to be better manipulated within the speculum support.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention handle assembly can be embodied in many ways, only a few exemplary embodiments are illustrated. The exemplary embodiments are being shown for the purposes of explanation and description. The exemplary embodiments are selected in order to set forth some of the best modes contemplated for the invention. The illustrated embodiments, however, are merely exemplary and should not be considered as limiting when interpreting the scope of the claims.

Figure 1:
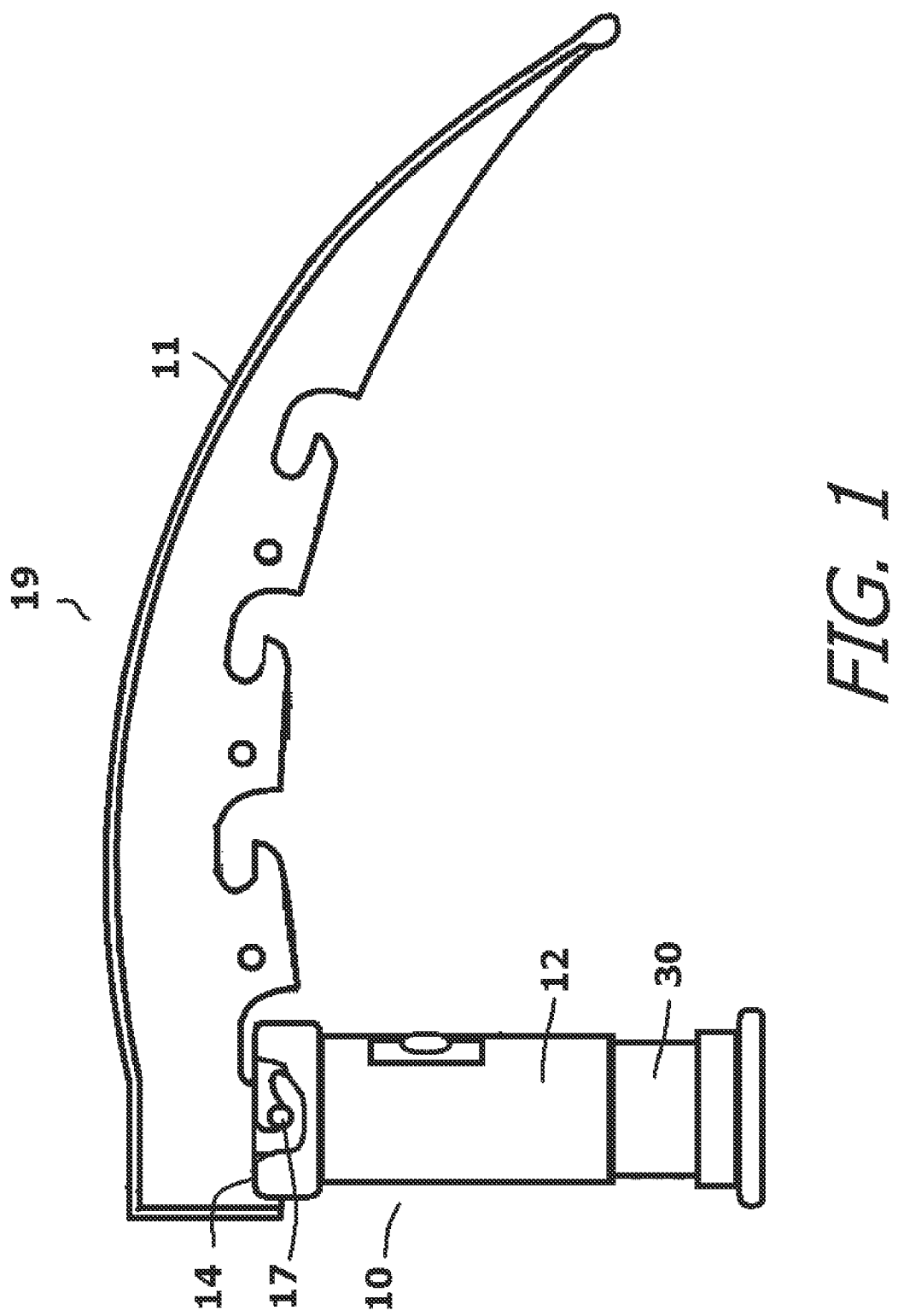
FIG. 1 shows an exemplary embodiment of a handle assembly in conjunction with a laryngoscope blade to form a laryngoscope.

Referring to FIG. 1, a multipurpose handle assembly 10 is shown in conjunction with a laryngoscope blade 11 in a traditional application and configuration. The handle assembly 10 has a top end 14. A connector 17 is formed at the top end 14 that conforms to the specifications of ISO 7376.7. The multipurpose handle assembly 10 attaches to the laryngoscope blade 11, therein forming a traditional laryngoscope 19 that can be held and manipulated using the multipurpose handle assembly 10. The multipurpose handle assembly 10 also has use as a medical instrument separate and apart from laryngoscope blade 11.

Figure 2:
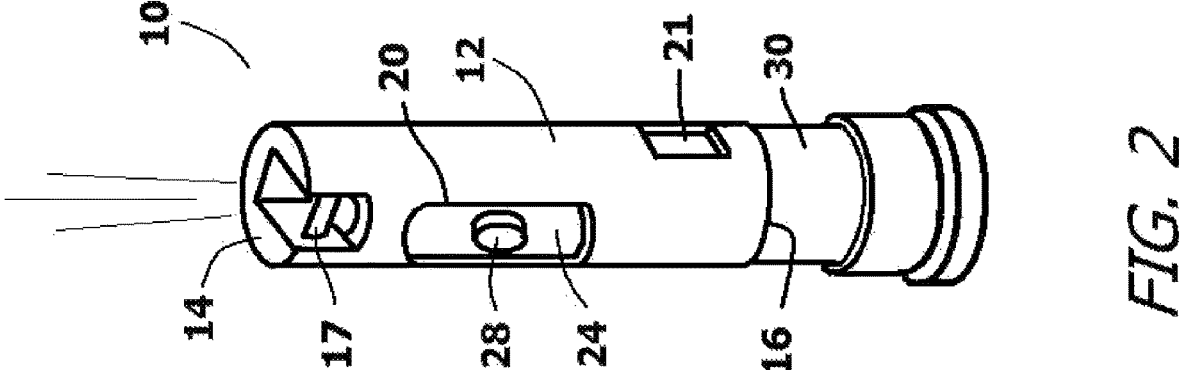
FIG. 2 shows a perspective view of the handle assembly used in FIG. 1.
Figure 3:
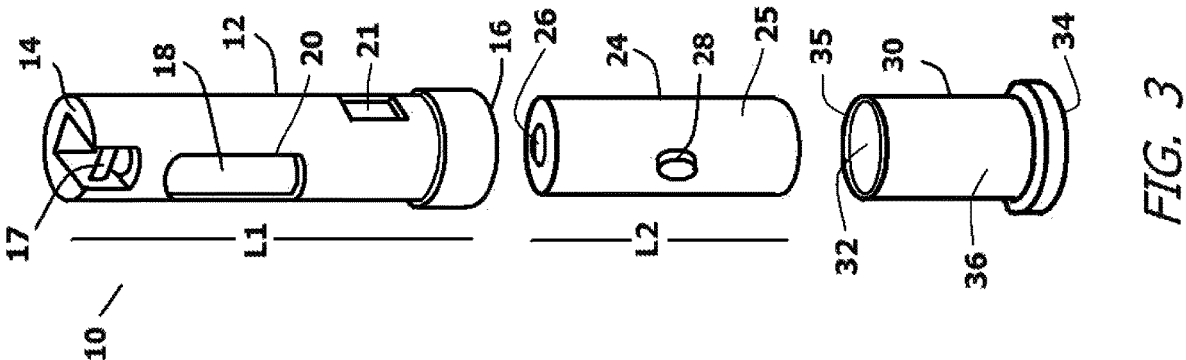
FIG. 3 is an exploded perspective view of the handle assembly shown in FIG. 2.

Referring to FIG. 2 in conjunction with FIG. 3, it can be seen that the handle assembly 10 has a primary body 12 that is made of molded plastic. The primary body 12 has a top end 14, an opposite bottom end 16, and a length L1 between the top end 14 and the bottom end 16. As previously stated, a standard ISO 7376.7 connector 17 is formed into the top end 14 of the primary body 12. The primary body 12 defines an open central cavity 18 between the top end 14 and the bottom end 16. The open central cavity 18 is accessible through the bottom end 16 and various access windows 20, 21 that are formed in the primary body 12.

The open central cavity 18 within the primary body 12 is sized and shaped to receive a separate and distinct flashlight unit 24. The flashlight unit 24 contains its own housing 25 that encases an LED light 26, an internal battery, and an activation switch 28. The housing 25 has a length L2, which is shorter than the length L1 of the primary body 12. The activation switch 28 can be a button on the flashlight unit 24 that aligns with the first access window 20 in the primary body 12. Alternatively, the activation switch 28 can be a twist switch on the flashlight unit 24 that aligns with the second access window 21 in the primary body 12. In this manner, flashlight units 24 of different types can be placed inside the primary body 12, while still being operational from outside the primary body 12. Accordingly, the flashlight unit 24 can be any commercially available flashlight unit that is capable of fitting within the open central cavity 18 and having an activation switch 28 that aligns with one of the access windows 20, 21.

When the flashlight unit 24 is positioned within the primary body 12, the flashlight unit 24 shines light toward, and beyond, the laryngoscope connector 22. This light can be redirected through a laryngoscope blade and used for illumination. As previously stated, the flashlight unit 24 has a length that is shorter than the length of the primary body 12. Accordingly, there is extra space in the open central cavity 18 of the handle assembly 10 after the flashlight unit 24 is positioned. The extra space in the primary body 12 is sized to accommodate a detachable housing extension 30.

The detachable housing extension 30 passes inside the primary body 12 through the open bottom end 16 of the primary body 12. The housing extension 30 defines an internal compartment 32 having a closed bottom end 34 and an open top end 35. The internal compartment 32 is capable of holding one or more secondary objects. The secondary objects can be medical related, such as sutures, medications, ointments, scalpel blades or the like. The housing extension 30 can have some external threading 36 or another similar connector that enables the housing extension 30 to mechanically engage the primary body 12 when inserted into the open bottom end 16 of the primary body 12. In this manner, the housing extension 30 can selectively interconnect with the primary body 12 and will not inadvertently fall away from the primary body 12 as the handle assembly 10 is maneuvered.

Figure 4:
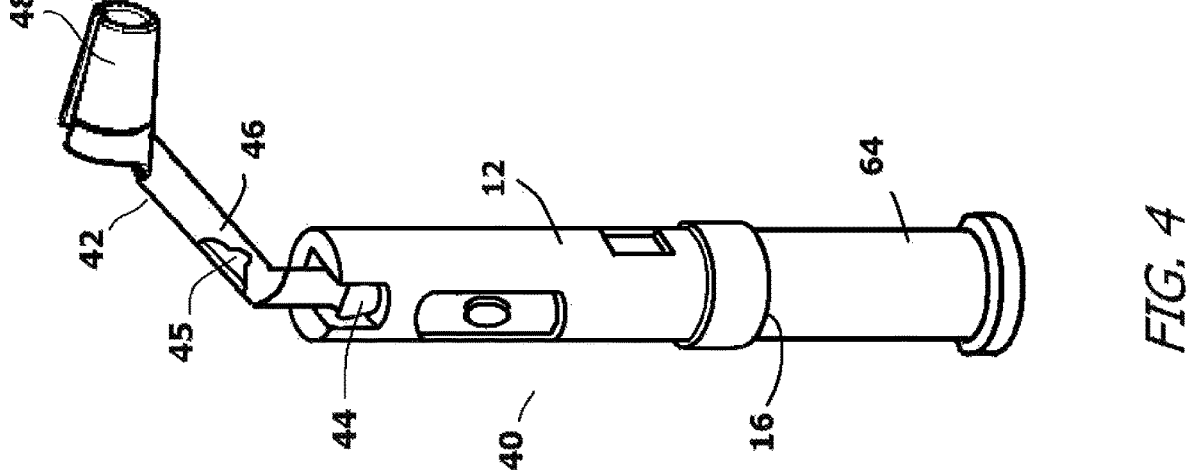
FIG. 4 shows an alternate configuration for the handle assembly, wherein the handle assembly is part of an otoscope.
Figure 5:
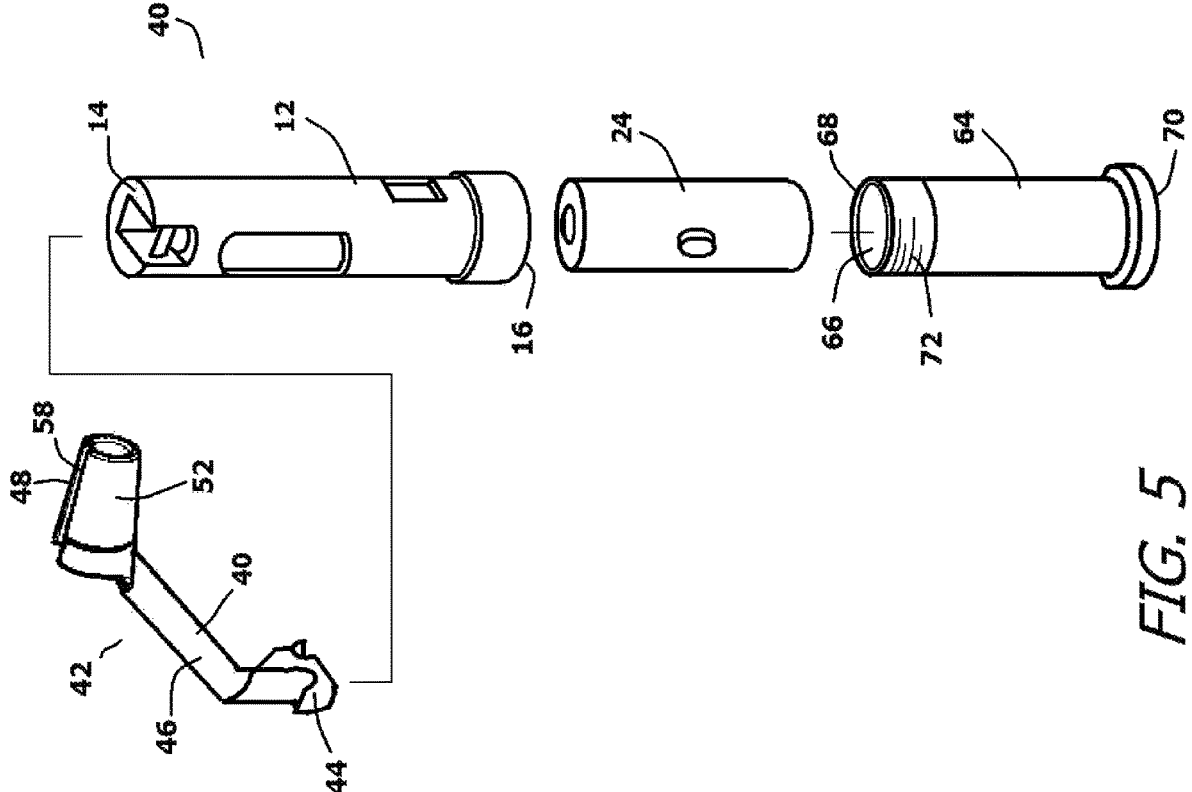
FIG. 5 is an exploded view of the alternate configuration shown in FIG. 4.

The connector 17 at the top end 14 of the primary body 12 is made to the ISO 7376.7 standard to enable engagement with a laryngoscope blade. Other medical instruments can also be made with ISO standard connections. Referring to FIG. 4 and FIG. 5, a handle assembly 40 is shown that has the same primary body 12 previously described in FIG. 2 and FIG. 3. Accordingly, the same reference numbers are used to describe the primary body 12 and its components. In FIG. 4 and FIG. 5, it can be seen that the handle assembly 40 is used to manipulate a specialized otoscope head 42. The otoscope head has a base 44, a neck 46 and a speculum support 48. The base 44 is configured with a connector 50 that meets the ISO 7376.7 standard. Accordingly, the base 44 of the otoscope head 42 connects to the connector 17 on the primary body 12 in the same manner as would a laryngoscope blade. The primary body 12 holds a flashlight unit 24 in the same manner as has been previously described. The otoscope head 42 contains a fiber optic pathway 45 that extends through the neck 46 from the base 44 to the speculum support 48. Light from the flashlight unit 24 is received by the fiber optic pathway 45 and is directed to the speculum support 48. The light is then used to illuminate a pathway ahead of the speculum support 48.

Figure 6:
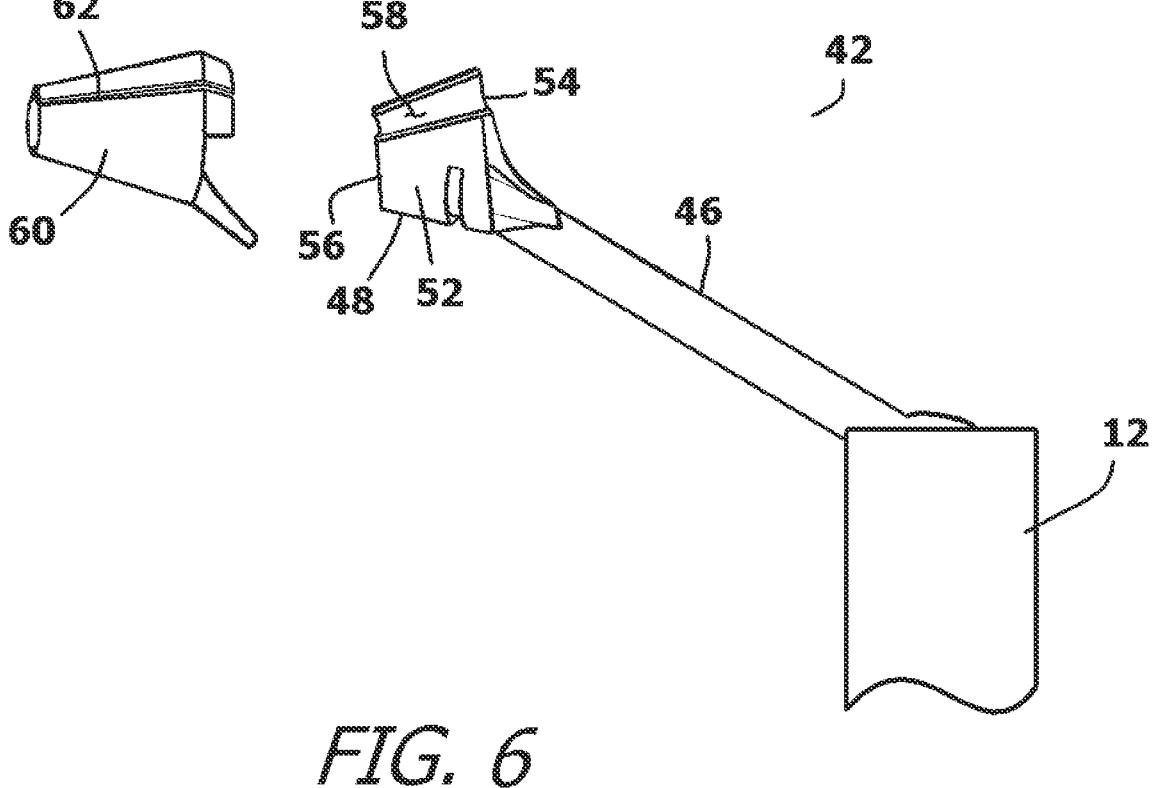
FIG. 6 is an enlarged view of an improved otoscope head engaging the handle assembly.

Referring to FIG. 6 in conjunction with FIG. 5, it can be seen that the otoscope head 42 contains an elongated neck 46 that terminates with a speculum support 48. The speculum support 48 has a funnel shaped peripheral wall 52 that extends between a large open end 54 and a small open end 56. The elongated neck 46 attaches to the funnel shaped peripheral wall 52 at a point between the large open end 54 and said small open end 56. The peripheral wall 52 is not continuous. Rather, a slot 58 is formed in the peripheral wall 52 that extends from the large open end 54 to the small open end 56. The slot 58 enables tweezers, probes, and other instruments to be better used in conjunction with the otoscope head 42. Disposable speculum caps 60 can be provided. The disposable speculum caps 60 connect over the speculum support 48. Each disposable speculum cap 60 also contains slots 62 that align with the slot 58 of the speculum support 48 when the disposable speculum cap 54 is placed over the speculum support 48.

The otoscope head 42 is small enough to be held within the handle assembly 10. Returning to FIG. 4 and FIG. 5, it can be seen that a body extension 64 is attached to the bottom end 16 of the primary body 12. The body extension 64 defines an internal compartment 66 between an open top 68 and a closed bottom 70. The internal compartment 66 is sized to receive and store the otoscope head 42 therein when not in use. For use, the otoscope head 42 is removed from the body extension 64 and attached to the top end 14 of the primary body 12.

The body extension 64 can have some external threading 72 or another similar connector that enables the body extension 64 to mechanically engage the primary body 12. In this manner, the body extension 64 can selectively interconnect with the primary body 12 and will not inadvertently fall away from the primary body 12 as the overall handle assembly 10 is maneuvered.

It will be understood that the longer body extension 64 enables larger secondary objects to be held in in the handle assembly 40, should the otoscope head 52 not be present. Such secondary objects include, but are not limited to, scalpel heads, sutures, bandages, forceps, clamps, tweezers, swabs, tongue depressors, rongeurs and speculums.

The embodiments of the present invention that are illustrated and described are merely exemplary and it will be understood that a person skilled in the art can make many variations to those embodiments. All such embodiments are intended to be included within the scope of the present invention as defined by the below claims.

What is claimed is:

1. A handle assembly for a medical instrument, comprising:

a primary housing having a first end and an opposite open second end, wherein said primary housing defines an open central cavity, and wherein said open central cavity is accessible through said open second end and at least one access opening that is disposed between said first end and said open second end;

a connector formed at said first end of said primary housing;

a selectively detachable housing extension attached to said open second end of said primary housing, wherein said housing extension defines an internal compartment that is accessible when said housing extension is detached from said primary housing; and an otoscope head that is sized to fit within said internal compartment of said housing extension.

2. The handle assembly according to claim 1, wherein said otoscope head has a base, a neck, and a speculum support, wherein said base is configured to interconnect with said connector at said first end of said primary housing.

3. The handle assembly according to claim 2, wherein said speculum support has a large open end, an opposite small open end and a funnel shaped peripheral wall that extends from said large open end to said small open end, wherein said neck attaches to said funnel shaped peripheral wall at a point between said large open end and said small open end.

4. The handle assembly according to claim 3, further including an access slot formed in said funnel shaped peripheral wall that extends from said large open end to said small open end.

5. The handle assembly according to claim 1, further including a flashlight unit that is received within said open central cavity of said primary housing.

6. The handle assembly according to claim 5, wherein said flashlight unit is accessible in said primary housing through said at least one access opening.

7. The handle assembly according to claim 6, further including an otoscope head attached to said connector on said primary housing, wherein said flashlight unit produces light that is channeled through said otoscope head.

8. An otoscope assembly comprising:

a handle assembly having a connector at one end, wherein said handle assembly includes a primary housing having a first end and an opposite open second end;

a selectively detachable housing extension attached to said open second end of said primary housing, wherein said housing extension defines an internal compartment that is accessible when said housing extension is detached from said primary housing; and an otoscope head having a base, a neck, and a speculum support, wherein said base is configured to interconnect with said connector of said handle assembly and wherein said otoscope head is sized to fit within said internal compartment.

9. The assembly according to claim 8, wherein said speculum support has a large open end, an opposite small open end and a funnel shaped peripheral wall that extends from said large open end to said small open end, wherein said neck attaches to said funnel shaped peripheral wall at a point between said large open end and said small open end.

10. The assembly according to claim 9, further including an access slot formed in said funnel shaped peripheral wall that extends from said large open end to said small open end.

11. The assembly according to claim 8, further including a flashlight unit that is received within said primary housing.

12. The assembly according to claim 11, wherein said flashlight unit produces light that is channeled through said otoscope head.

* * * * *